US012420040B2

(12) United States Patent
Skinner

(10) Patent No.: US 12,420,040 B2
(45) Date of Patent: Sep. 23, 2025

(54) SURGICAL RETENTION APPARATUS

(71) Applicant: Allevo Veterinary Solutions LLC, San Diego, CA (US)

(72) Inventor: Allen Skinner, San Diego, CA (US)

(73) Assignee: Allevo Veterinary Solutions LLC, San Diego, CA (US)

( * ) Notice: Subject to any disclaimer, the term of this patent is extended or adjusted under 35 U.S.C. 154(b) by 24 days.

(21) Appl. No.: 18/527,349

(22) Filed: Dec. 3, 2023

(65) Prior Publication Data

US 2024/0165352 A1 May 23, 2024

Related U.S. Application Data

(63) Continuation-in-part of application No. 17/469,919, filed on Sep. 9, 2021.

(51) Int. Cl.
*F16M 11/00* (2006.01)
*A61M 16/01* (2006.01)

(52) U.S. Cl.
CPC ....... *A61M 16/01* (2013.01); *A61M 2209/082* (2013.01)

(58) Field of Classification Search
CPC ............ A61M 16/01; A61M 2209/082; A61M 16/0497; A61M 16/0875; A61M 2250/00; A61M 16/0003; A61G 13/101; A61D 11/00; A61D 3/00
USPC ........................................................... 248/75
See application file for complete search history.

(56) References Cited

U.S. PATENT DOCUMENTS

| 4,312,352 | A | * | 1/1982 | Meisch | ..................... A61F 5/44 604/322 |
| 5,375,799 | A | * | 12/1994 | Rhodes | ................ A61G 7/0503 248/215 |
| 11,168,834 | B2 | * | 11/2021 | Roberts | .................... F16L 3/245 |
| 2017/0258984 | A1 | * | 9/2017 | Meyer | ..................... F16L 3/222 |
| 2024/0173503 | A1 | * | 5/2024 | Kanowitz | ......... A61M 16/0688 |

* cited by examiner

*Primary Examiner* — Amy J. Sterling
(74) *Attorney, Agent, or Firm* — Knobbe, Martens, Olson & Bear, LLP

(57) ABSTRACT

Embodiments of the instant disclosure relate to surgical retention apparatuses. The apparatus includes a main body, loop, and coupler. The main body includes a top, bottom and the coupler. The loop is symmetrically coupled to the top. The coupler is positioned near the bottom and configured to couple the main body to an object. The coupler is accessible from the bottom. The main body, loop, and/or coupler includes a metal or polymer. The main body is planar. The loop includes an angular planar surface. The coupler includes a tab that extends from the main body, is oriented parallel to the main body, and is oriented towards the bottom. The main body includes parallel voids that extend from the bottom to form the coupler. The loop includes a planar appendage that extends from the top and curvingly terminates at the top to form an aperture and couple to the main body.

18 Claims, 7 Drawing Sheets

SURGICAL RETENTION APPARATUS

BACKGROUND

The present invention relates generally to retaining apparatuses and specifically to surgical retaining apparatuses. Veterinary examination tables are known in the art for supporting a patient thereon while a veterinary professional examines the patient or performs a medical procedure. Conventional veterinary examination tables typically include a generally flat patient support surface.

Patient safety is paramount when performing procedures. One way to enhance patient safety is to ensure that anesthesia tubing supplied to the patient does not fall off the side of the procedure table. Unfortunately, if such an event were to occur, the weight of the anesthesia tubing subsequently pulls on the endotracheal tube (i.e., the tube that is lodged in the patient's mouth and extends down into the trachea) and potentially wrenches the endotracheal tube out of the patient's mouth or injure the patient. Consumers would benefit from retaining apparatuses for examination tables that help retain anesthesia tubing and thereby enhance patient safety.

DETAILED DESCRIPTION

Figure 1:
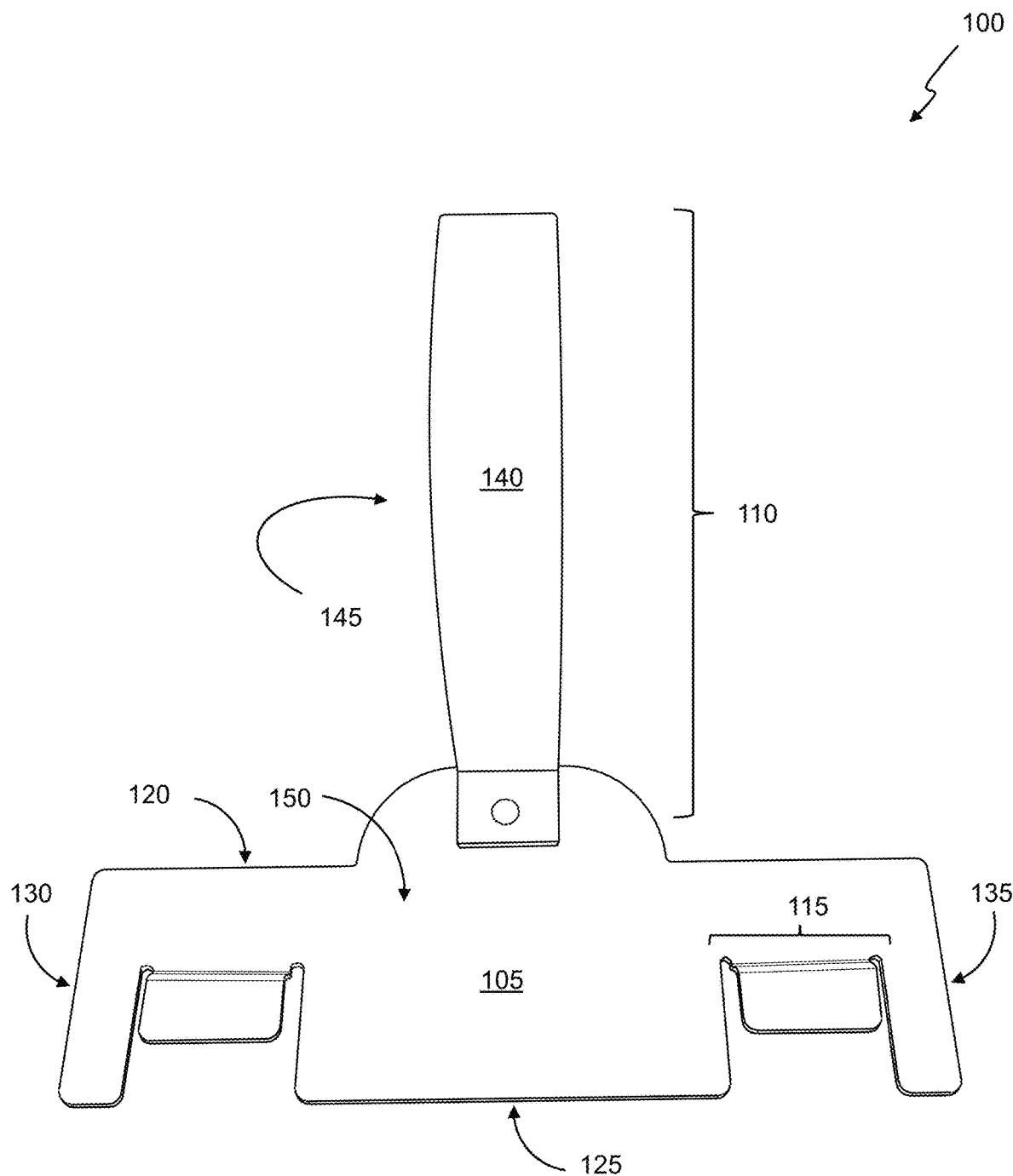
FIG. 1 depicts a front view of a surgical retention apparatus, in accordance with some embodiments.
Figure 2:
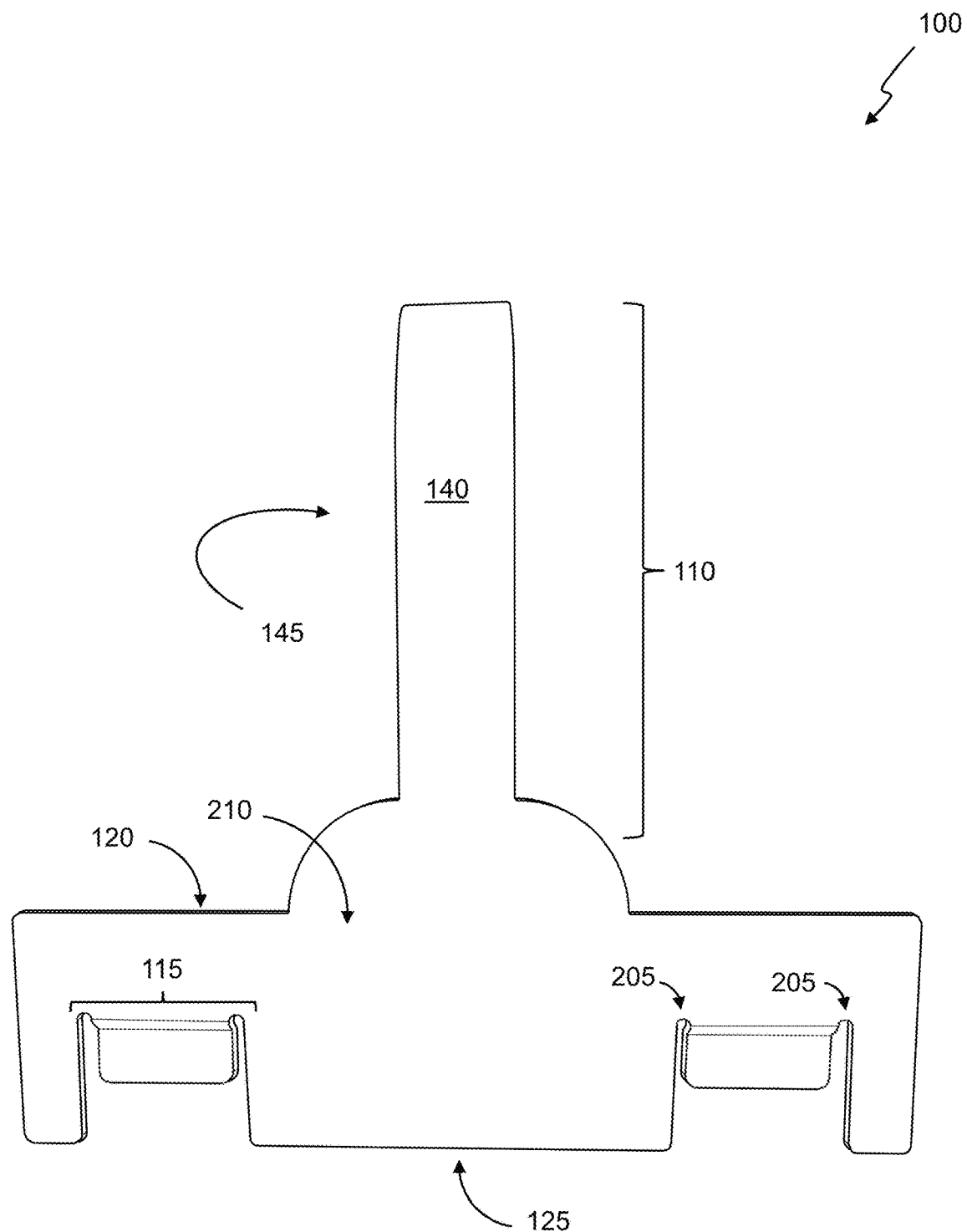
FIG. 2 depicts a rear view of the surgical retention apparatus of FIG. 1, in accordance with other embodiments.
Figure 3:
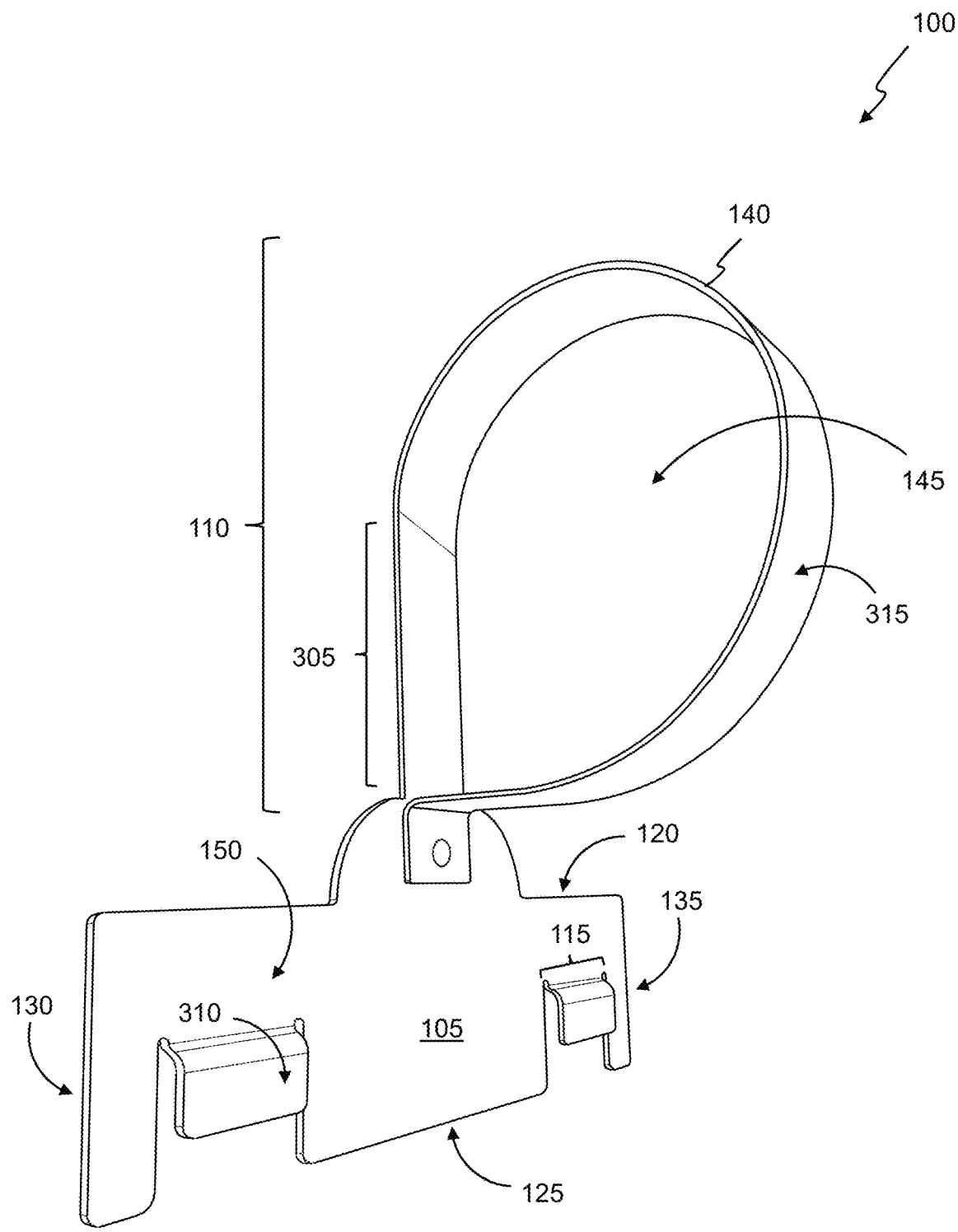
FIG. 3 depicts a left perspective view of the surgical retention apparatus of FIG. 1, in accordance with certain embodiments.
Figure 4:
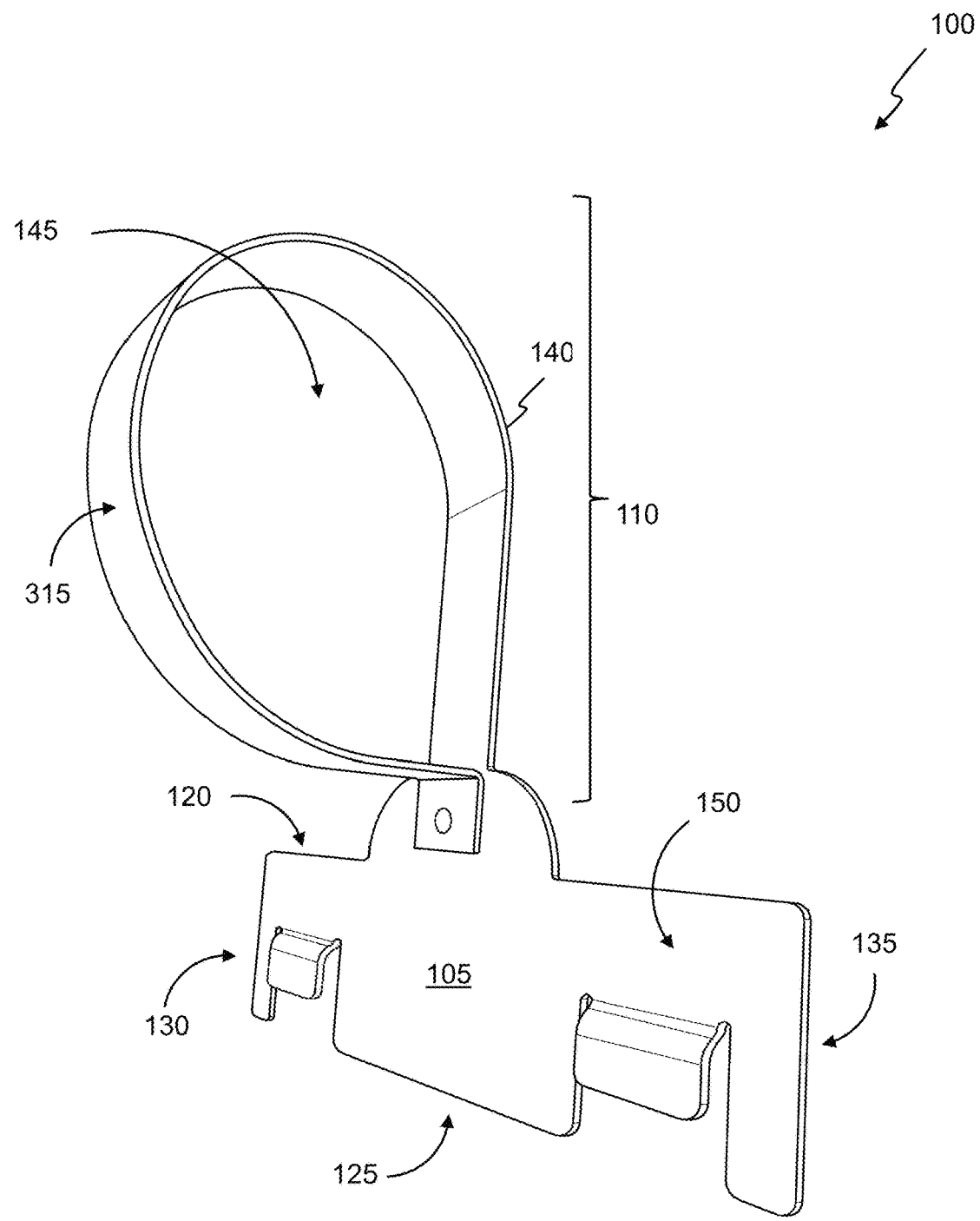
FIG. 4 depicts a right perspective view of the surgical retention apparatus of FIG. 1, in accordance with yet still other embodiments.
Figure 5:
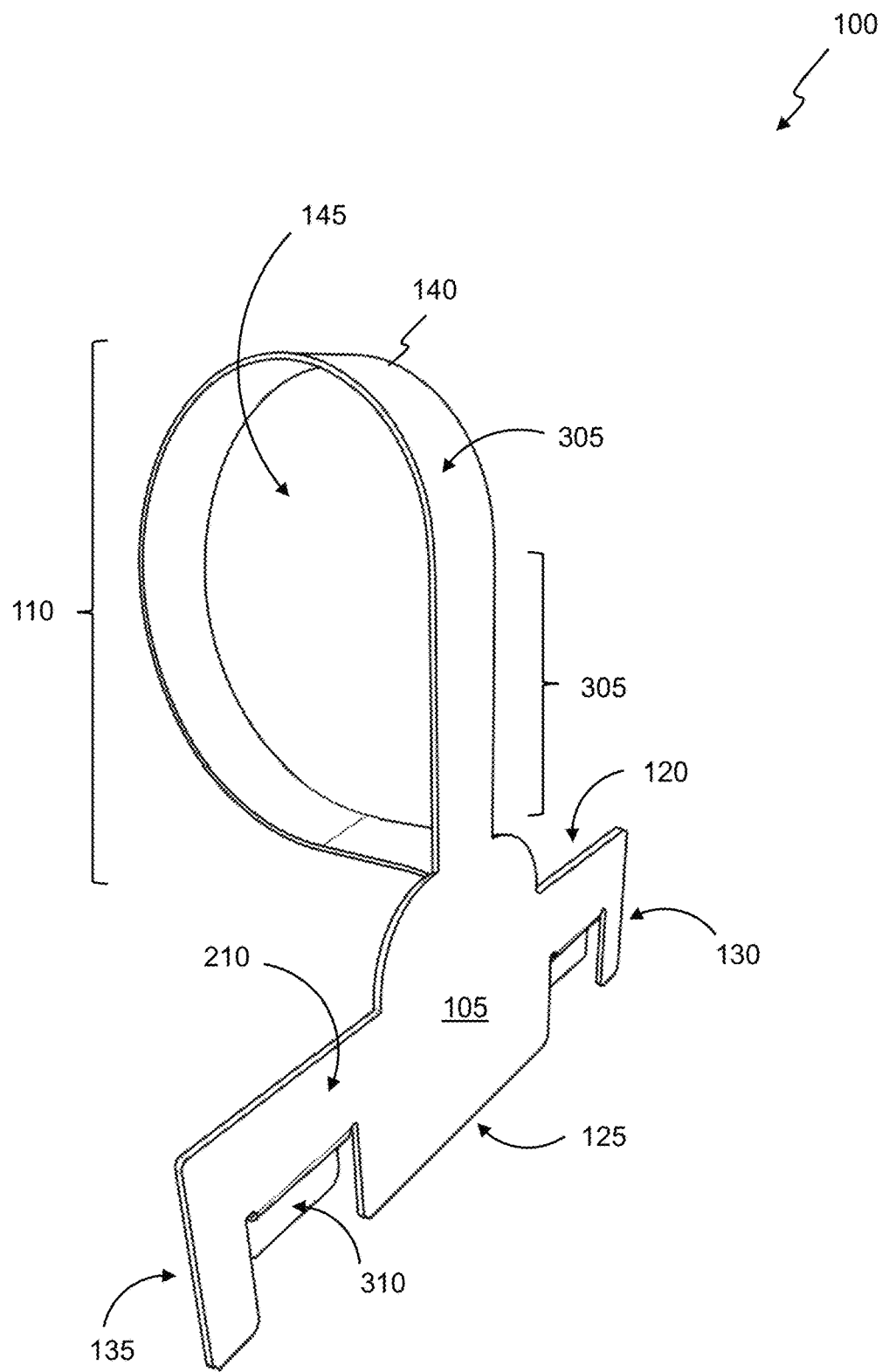
FIG. 5 depicts a rear perspective view of the surgical retention apparatus of FIG. 1, in accordance with some embodiments.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Certain terminology may be employed in the following description for convenience rather than for any limiting purpose. For example, the terms "forward" and "rearward," "front" and "rear," "right" and "left," "upper" and "lower," and "top" and "bottom" designate directions in the drawings to which reference is made, with the terms "inward," "inner," "interior," or "inboard" and "outward," "outer," "exterior," or "outboard" referring, respectively, to directions toward and away from the center of the referenced element, the terms "radial" or "horizontal" and "axial" or "vertical" referring, respectively, to directions or planes which are perpendicular, in the case of radial or horizontal, or parallel, in the case of axial or vertical, to the longitudinal central axis of the referenced element, the terms "proximate" and "distal" referring, respectively, to positions or locations that are close or away from a point of reference, and the terms "downstream" and "upstream" referring, respectively, to directions in and opposite that of fluid flow. Terminology of similar import other than the words specifically mentioned above likewise is to be considered as being used for purposes of convenience rather than in any limiting sense.

In the figures, elements having an alphanumeric designation may be referenced herein collectively or in the alternative, as will be apparent from context, by the numeric portion of the designation only. Further, the constituent parts of various elements in the figures may be designated with separate reference numerals which shall be understood to refer to that constituent part of the element and not the element as a whole. General references, along with references to spaces, surfaces, dimensions, and extents, may be designated with arrows. Angles may be designated as "included" as measured relative to surfaces or axes of an element and as defining a space bounded internally within such element therebetween, or otherwise without such designation as being measured relative to surfaces or axes of an element and as defining a space bounded externally by or outside of such element therebetween. Generally, the measures of the angles stated are as determined relative to a common axis, which axis may be transposed in the figures for purposes of convenience in projecting the vertex of an angle defined between the axis and a surface which otherwise does not extend to the axis. The term "axis" may refer to a line or to a transverse plane through such line as will be apparent from context.

Veterinary examination tables are known in the art for supporting a patient thereon while a veterinary professional examines the patient or performs a medical procedure. Conventional veterinary examination tables typically include a generally flat patient support surface. Patient safety is paramount when performing procedures. One way to enhance patient safety is to ensure that anesthesia tubing supplied to the patient does not fall off the side of the procedure table. Unfortunately, if such an event were to occur, the weight of the anesthesia tubing subsequently pulls on the endotracheal tube (i.e., the tube that is lodged in the patient's mouth and extends down into the trachea) and potentially wrenches the endotracheal tube out of the patient's mouth or injure the patient. Consumers would benefit from retaining apparatuses for examination tables that help retain anesthesia tubing and thereby enhance patient safety.

Embodiments of the instant disclosure seek to provide surgical retention apparatuses that can demountably attach to objects (e.g., veterinary wet tables and similar medical supporting surfaces). Other embodiments of the instant disclosure seek to provide surgical retention apparatuses that can selectively retain medical objects that are common to procedure spaces to facilitate and enhance the organization and tidiness thereof.

Turning now to the Figures FIGS. 1-5 depict various views of a surgical retention apparatus ("apparatus"), generally 100, according to some embodiments. Specifically, FIGS. 1-5 depict a front view, rear view, left perspective view, right perspective view, and rear perspective view, respectively, of the apparatus 100. The apparatus 100 is a retaining attachment that demountably attaches to a patient supporting surface (e.g., a wet table) to facilitate and enhance organization and tidiness. The apparatus 100 can include a main body 105, a loop 110, and a coupler 115. Although the main body 105, the loop 110, and the coupler 115 can be made of or include a polymer (e.g., polyvinyl chloride, polyethylene terephthalate, and similar thermoplastics), such components preferably are metallic to promote sanitation. In other words, the main body 105, the loop 110, and the coupler 115 can include a metal and/or a polymer. To be sure, metals and alloys, including stainless steel, titanium and its alloys and cobalt alloys, have been widely used clinically due to their high strength, good wear resistance, good corrosion resistance, high fatigue properties and good biocompatibility.

The apparatus 100 has an attachment portion (i.e., the main body 105) that selectively attaches the apparatus 100 to an object and a retaining portion (i.e., the loop 110) that selectively retains medical objects and accessories that are common to procedure spaces (e.g., tubing and similar medical objects that can be draped or hung). The main body 105 and the loop 110 can be formed separately and subsequently coupled together. Alternatively, the main body 105 and the loop 110 can be formed as a single unit. The main body 105 can include a coupler 115, a top 120, a bottom 125, a side 130, and a side 135. In preferred embodiments, the main body 105 is structurally polygonal and/or substantially planar.

The loop 110 is preferably symmetrically coupled to the top 120 to ensure equal weight distribution of the apparatus 100 and reduce the probability of the coupler 115. Alternatively, the loop 110 can be asymmetrically coupled to the top 120 (i.e., positioned proximate to the side 130 or the side 135). The loop 110 can include an angular planar surface 315. In preferred embodiments, a portion of the loop 110 is oriented parallel with the main body 105. For example, the loop 110 includes a planar appendage 140 that longitudinally extends from the top 120 and then curvingly terminates proximate to the top 120 and a first face 150 of the main body 105 to thereby form an aperture 145, which receives the procedure room accessories to be retained. The first face 150 is preferably oriented opposite a second face 210 of the main body 105.

The main body 105 preferably includes parallel voids 205 that extend from the bottom 125 towards the top 120 in a manner to thereby form the coupler 115. Alternatively, the main body 105 does not include the parallel voids 205 and the coupler 115 is coupled to the first face 150 as aforementioned. The coupler 115 can be positioned proximate to the bottom 125 (e.g., to provide leverage for the apparatus 100) and configured to selectively couple the main body 105 to an object (e.g., the wet table 605). The coupler 115 is preferably accessible from the bottom 125, which allows the main body 105 and the coupler 115 to rest on opposite sides of a receiving slot (e.g., receiving slot 610) positioned on the object (e.g., the wet table 605). To be sure, the coupler 115 and the receiving slot have complementary structures. In certain embodiments, the coupler 115 includes a tab 310 that extends ventrally from the main body 105 (i.e., away from the first face 150) in a manner to be oriented parallel to the main body 105 and towards the bottom 125. In other words, the coupler 150 preferably perpendicularly extend from the main body 105 and is angularly oriented towards the bottom 125. The coupler 115 can be positioned proximate to the side 130 or the side 135.

Figure 6:
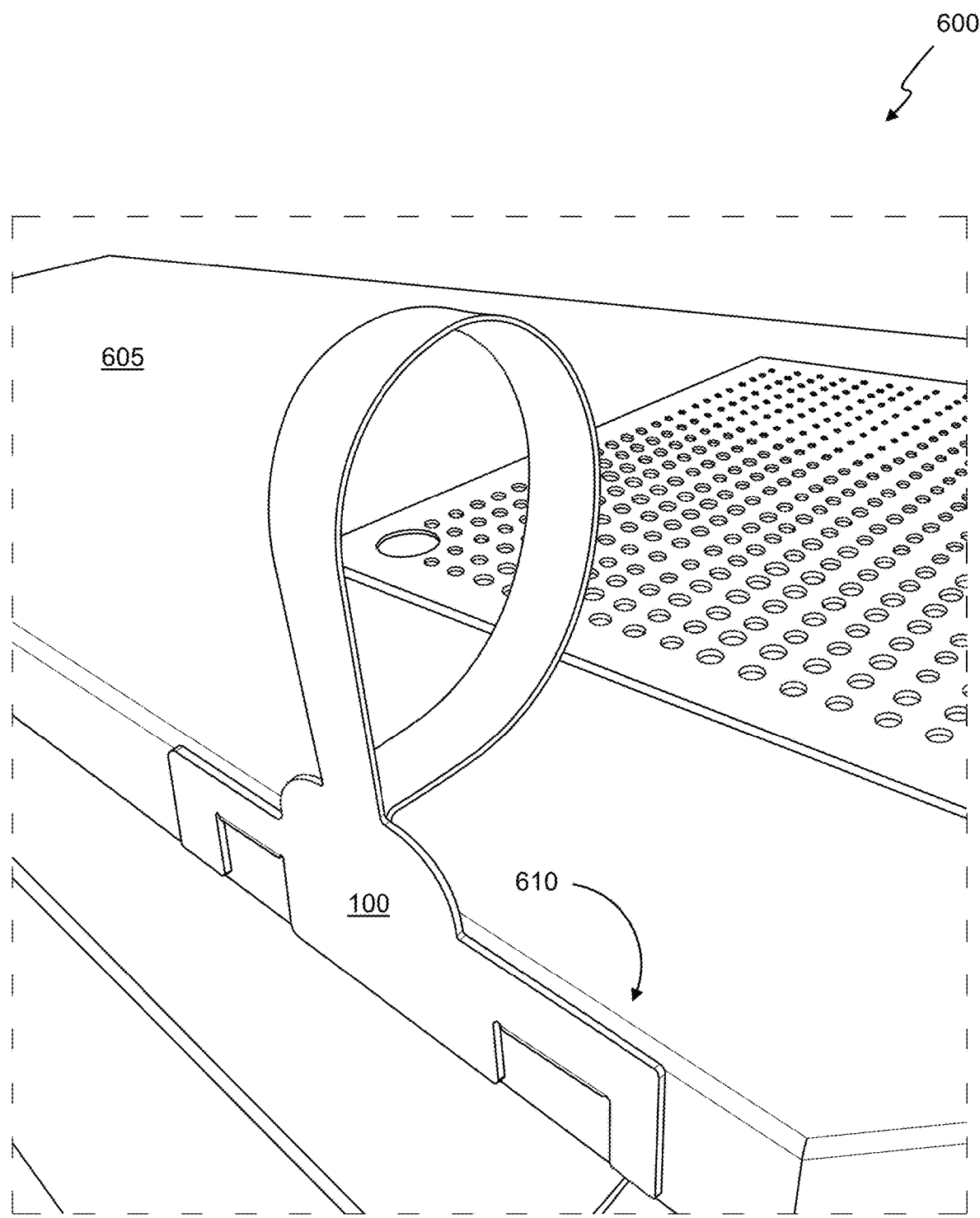
FIG. 6 illustrates a picture of the surgical retention apparatus of FIG. 1 in an "empty state" while attached to a wet table, in accordance with other embodiments.
Figure 7:
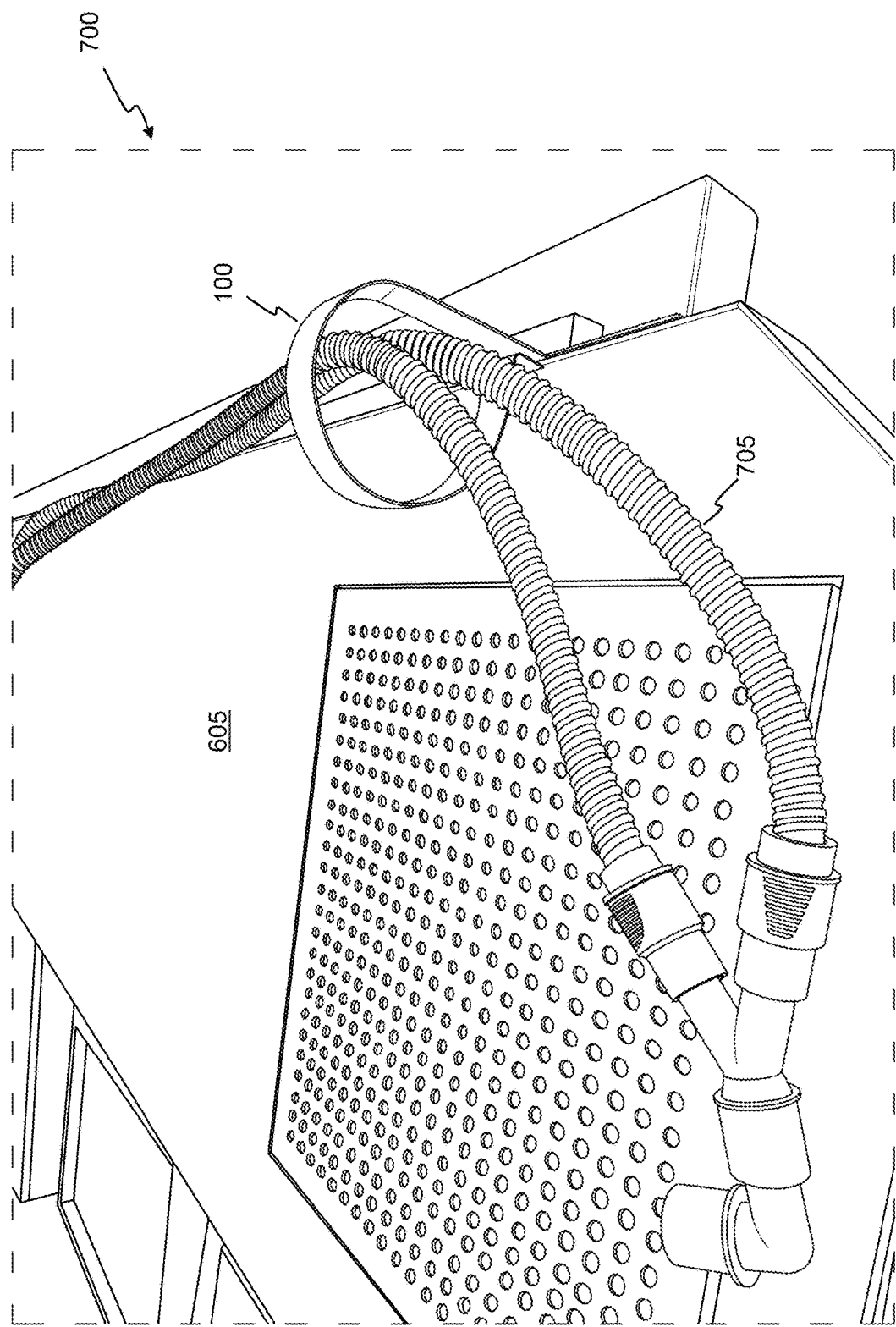
FIG. 7 illustrates the picture of FIG. 6 with the surgical retention apparatus of FIG. 1 in a "retaining state" while attached to the wet table, in accordance with certain embodiments.

Turning now to FIGS. 6 and 7. Here, the apparatus 100 is depicted as being coupled to a side of the wet table 605. The apparatus 100 is depicted in its "empty state" (FIG. 6) and "retaining state (FIG. 7). In the "empty state," the aperture 145 is free of any objects to retain. In the "retaining state," an object (e.g., a tubing 705) is present within the aperture 145 and is thereby retained to a predetermined area of the wet table 605.

Based on the foregoing, surgical retention apparatuses have been disclosed herein. However, numerous modifications and substitutions can be made without deviating from the scope of the instant disclosure. Therefore, the instant disclosure has been provided by way of example and not limitation.

What is claimed is:

1. A surgical retention apparatus, comprising:
    a main body comprising at least one coupler positioned proximate a bottom of the main body, the coupler configured to removably attach the surgical retention apparatus to a support surface; and
    a loop, a first portion of the loop being substantially parallel to the main body and extending outward from the top of the main body and a second portion of the loop curving from the first portion to the top of the main body, the loop configured to retain medical objects,
    wherein the support surface is a wet table.

2. The surgical retention apparatus of claim 1, wherein the main body is substantially planar.

3. The surgical retention apparatus of claim 1, wherein the first portion of the loop and the second portion of the loop form an aperture.

4. The surgical retention apparatus of claim 1, wherein the at least one coupler comprises a tab, the tab extending ventrally from the main body and towards a bottom of the main body, and wherein the tab is oriented parallel to the main body.

5. The surgical retention apparatus of claim 1, wherein the main body comprises parallel voids that extend from the bottom of the main body towards the top of the main body, at least a portion of the at least one coupler being formed by the parallel voids.

6. The surgical retention apparatus of claim 1, wherein the first portion of the at least one coupler perpendicularly extends from the main body and the second portion of the at least one coupler is angularly oriented towards the bottom of the main body.

7. The surgical retention apparatus of claim 1, wherein the main body comprises at least one side, and wherein the at least one coupler is positioned proximate to the at least one side.

8. The surgical retention apparatus of claim 1, wherein the loop and the main body are integrally formed.

9. The surgical retention apparatus of claim 1, wherein the loop is positioned centrally along a length of the main body.

10. A surgical retention apparatus, comprising:
    a main body comprising at least one coupler positioned proximate a bottom of the main body, the coupler configured to removably attach the surgical retention apparatus to a support surface; and
    a loop, a first portion of the loop being substantially parallel to the main body and extending outward from the top of the main body and a second portion of the loop curving from the first portion to the top of the main body, the loop configured to retain medical objects, wherein the loop is positioned along a length of the main body such that the loop is positioned closer to a first side of the main body than to a second side of the main body.

11. The surgical retention apparatus of claim 1, wherein the main body is metallic.

12. The surgical retention apparatus of claim 1, wherein the loop is metallic.

13. The surgical retention apparatus of claim 1, wherein the at least one coupler comprises a first couple and a second coupler, and wherein the first coupler is located proximate a first side of the main body and the second coupler is located proximate a second side of the main body.

14. The surgical retention apparatus of claim 13, wherein the first coupler and the second coupler are located symmetrically along a length of the main body.

15. The surgical retention apparatus of claim 13, wherein the loop is positioned between the first coupler and the second coupler.

16. The surgical retention apparatus of claim 13, wherein the second portion of the loop, the first coupler, and the second coupler extend from a front face of the main body, and wherein a rear face of the main body is substantially planar.

17. The surgical retention apparatus of claim 1, further comprising the support surface.

18. The surgical retention apparatus of claim 1, wherein the support surface comprises one or more slots configured to receive the at least one coupler.

\* \* \* \* \*